(12) United States Patent
Deshpande et al.

(10) Patent No.: US 9,469,575 B2
(45) Date of Patent: *Oct. 18, 2016

(54) NON-REDUCTIVE DEHYDROXYLATION OF VICINAL COMPOUNDS TO OLEFINS USING A HALOGEN-BASED CATALYST

(71) Applicant: Dow Global Technologies LLC, Midland, MI (US)

(72) Inventors: Raj Deshpande, Pune (IN); Paul Davis, Pune (IN); Vandana Pandey, Pune (IN); Nitin Kore, Solapur (IN)

(73) Assignee: Dow Global Technologies LLC, Midland, MI (US)

( * ) Notice: Subject to any disclaimer, the term of this patent is extended or adjusted under 35 U.S.C. 154(b) by 207 days.

This patent is subject to a terminal disclaimer.

(21) Appl. No.: 14/364,703

(22) PCT Filed: Dec. 5, 2012

(86) PCT No.: PCT/US2012/067834
§ 371 (c)(1),
(2) Date: Jun. 12, 2014

(87) PCT Pub. No.: WO2013/090074
PCT Pub. Date: Jun. 20, 2013

(65) Prior Publication Data
US 2014/0378730 A1  Dec. 25, 2014

Related U.S. Application Data

(60) Provisional application No. 61/570,956, filed on Dec. 15, 2011.

(51) Int. Cl.
C07C 1/22 (2006.01)
C07C 1/213 (2006.01)
C07C 1/24 (2006.01)

(52) U.S. Cl.
CPC ............... *C07C 1/22* (2013.01); *C07C 1/213* (2013.01); *C07C 1/24* (2013.01); *C07C 2527/08* (2013.01)

(58) Field of Classification Search
CPC ........... C07C 1/22; C07C 1/213; C07C 1/24; C07C 11/04
USPC ........................................................ 585/639
See application file for complete search history.

(56) References Cited

U.S. PATENT DOCUMENTS

| | | | |
|---|---|---|---|
| 3,781,222 A | 12/1973 | Raffinage Cie Francaise | |
| 3,957,900 A | 5/1976 | Weisang et al. | |
| 5,516,960 A * | 5/1996 | Robinson | C07C 1/20 568/671 |
| 2007/0215484 A1 | 9/2007 | Peterson et al. | |
| 2008/0216391 A1 | 9/2008 | Cortright et al. | |
| 2009/0299109 A1 | 12/2009 | Gruber et al. | |
| 2010/0069691 A1 | 3/2010 | Morschbacker | |
| 2010/0076233 A1 | 3/2010 | Cortright et al. | |
| 2010/0077655 A1 | 4/2010 | Bauldreay et al. | |

FOREIGN PATENT DOCUMENTS

| | | |
|---|---|---|
| EP | 0150832 A2 | 8/1985 |
| WO | 9418214 A1 | 8/1994 |
| WO | 2008/103480 A2 | 8/2008 |

OTHER PUBLICATIONS

Bradbury, "The Mechanism of the Reaction between Glycerol and Hydriodic Acid" Journal of the American Chemical Society 1952 74 (11), 2709-2712.*
P. Sarmah, et al., Regioselective Transformation of Allylic, Benzylic and Tertiary Alcohols into the Corresponding Iodides with Aluminum Triiodide: Deoxygenation of Vicinal Diols, Tetrahedron, 1989, pp. 3569-3574, vol. 45, No. 11.
N. Barua, et al., A New Method for Deoxygenation of Vicinal Diols, Tetrahedron Letters, 1982, pp. 1365-1366, vol. 23, No. 13.
J. Ziegler, et al., Inorganic Chemistry, 2009, pp. 9998-10000, vol. 48.
J. Hine, et al., The Mechanism of the Transformation of Vicinal Dihalides to Olefins by Reaction with Iodide Ion, Journal of the American Chemical Society, 1955, pp. 361-364, vol. 77.
E. Arceo, et al., An efficient didehydroxylation method for the biomass-derived polyols glycerol and erythritol. Mechanistic studies of a formic acid-mediated; deoxygenation , Chemical Communication, 2009, pp. 3357-3359.
E. Arceo, et al., Rhenium-Catalyzed Didehydroxylation of Vicinal Diols to Alkenes Using a Simple Alcohol as a Reducing Agent, Journal of the American Chemical Society, 2010, vol. 132, pp. 11408-11409.
V.V. Korshak, et al., High-molecular weight compounds. XXVIII. Action of hydriodic acid on ethylene glycol and its polyesters, Izvestiya Akademii Nauk, 1950, pp. 276-277, Moscow.
E. Erlenmeyer, Studies of the process of the action of hydrogen iodide on glycerin, Justus Liebigs Annalen der Chemie, 1866, vol. 139, No. 2, pp. 211-234.
M. Schlosser, Methoden der Organischen Chemie, 1972, pp. 195-202.
Verlag, Science of Synthesis, 2009, pp. 829-832, vol. 47b, Alkenes.
International Search Report and Written Opinion for PCT/US2012/067834, Mail Date Apr. 5, 2013, pp. 1-13.
International Report on Patentability for PCT/US2012/067834, Mail Date Mar. 31, 2014, pp. 1-14.
Response to the International Written Opinion and Chapter II Demand for PCT/US2012/067834, Dated Oct. 14, 2013, pp. 1-16.
Response to the International Written Opinion for PCT/US2012/067834, Dated Jan. 24, 2014, pp. 1-9.
G. Stavber, et al., Iodine induced transformations of alcohols under solvent-free conditions, Tetrahedron Letters, 2006, pp. 8463-8466, vol. 47.

* cited by examiner

*Primary Examiner* — In Suk Bullock
*Assistant Examiner* — Jason Chong
(74) *Attorney, Agent, or Firm* — Dinsmore & Shohl LLP

(57) ABSTRACT

Olefins may be produced by the non-reductive dehydroxylation of vicinal polyols and/or their respective esters, in a liquid reaction medium, under a substantially non-reductive atmosphere, in the presence of a halogen-based, preferably iodine-based, catalyst. The reaction medium may be aqueous, non-aqueous, or a combination thereof, and may in some embodiments include a solubility enhancing agent.

7 Claims, No Drawings

NON-REDUCTIVE DEHYDROXYLATION OF VICINAL COMPOUNDS TO OLEFINS USING A HALOGEN-BASED CATALYST

This application is a non-provisional application claiming priority from the U.S. Provisional Patent Application No. 61/570,956, filed on Dec. 15, 2011, entitled "NON-REDUCTIVE DEHYDROXYLATION OF VICINAL COMPOUNDS TO OLEFINS USING A HALOGEN-BASED CATALYST," the teachings of which are incorporated by reference herein as if reproduced in full hereinbelow.

This invention relates generally to the field of non-reductive dehydroxylation of polyols. More particularly, it is a process to accomplish such non-reductive dehydroxylation of vicinal polyols and their respective esters.

Sugar alcohols include a variety of polyols. Such are frequently encountered in the form of mixtures of these materials, often including, for example, ethylene glycol, propylene glycol, glycerol, sorbitol, and a variety of other polyols containing from 2 to 6 carbon atoms. While sugar alcohols often represent viable starting materials for a variety of commercially useful products, such as olefins, the difficulty in separating them from one another may make it consequently difficult to control the selectivity to the desired final product or product mix.

Researchers have addressed conversions of alcohol mixtures in many ways. For example, United States Patent Publication (US) 2010/0077655 (Baudrey, et al.) discloses use of a heterogeneous catalyst comprising a metal on a catalyst support in a deoxygenation step to form oxygenates (e.g., an alcohol, a ketone or an aldehyde).

US 2010/0076233 (Cortright, et al.) teaches processes and reactor systems for conversion of an oxygenated hydrocarbon, especially a water-soluble oxygenated hydrocarbon, to a paraffin used as a liquid fuel. The teachings include converting a water-soluble oxygenated hydrocarbon to an oxygenate (e.g. an alcohol, furan, ketone, aldehyde, carboxylic acid, diol, triol or another polyol), then dehydrating the oxygenate to an olefin. The deoxygenation catalyst is preferably a heterogeneous catalyst that comprises at least one metal on a catalyst support. The metals include one or more of Cu, Re, Fe, Ru, Ir, Co, Rh, Pt, Pd, Ni, Os, W, Ag and Au. The catalyst may also include one or more of Mn, Cr, Mo, V, Nb, Ta, Ti, Zr, Y, La, Sc, Zn, Cd, Sn, Ge, P, Al, Ga, In and Tl. See also US 2008/0216391 (Cortright, et al.).

United States Patent Publication (US) 2007/0215484 (Peterson, et al.) relates to a method of making hydrocarbons from polyalcohols (also known as "polyhydric alcohols" or "polyols") and carbohydrates (e.g., monosaccharides such as glucose, disaccharides such as sucrose, starches including polymers of alpha-D-glucose units such as amylase and amylopectin, and fibers such as cellulose-based polysaccharide fibers). The polyalcohols and carbohydrates are combined with hydroiodic acid (HI) in aqueous solution in an electrochemical cell to form the hydrocarbon and elemental iodine ($I_2$). A parallel reaction within the electrochemical cell reduces the $I_2$ to regenerate HI by reducing elemental iodine.

P. Sarmah, et al., in "Regioselective Transformation of Allylic, Benzylic and Tertiary Alcohols into the Corresponding Iodides with Aluminum Triiodide: Deoxygenation of Vicinal Diols," *Tetrahedron*, Vol. 45, No. 1-1 (1989), pp. 3569-3574, teach use of a stoichiometric amount of aluminum triiodide as a catalyst to convert vicinal diols to olefins.

N. Barua, et al., in "A New Method for Deoxygenation of Vicinal Diols,"*Tetrahedron Letters*, Vol. 23, No. 13 (1982), pp. 1365-1366, discusses conversion of cis- and trans-vicinal diols into olefins in a one-step reaction using a combination of chlorotrimethylsilane and sodium iodide, with sodium iodide being present in an amount in excess of what stoichiometry would indicate is necessary.

US 2009/0299109 (Gruber, et al.) focuses on dehydration of alcohols derived from a renewable material, e.g., by fermentation or chemical conversion of biomass. Dehydration occurs using a heterogeneous or homogeneous acidic catalyst. Illustrative catalysts include an acid treated aluminum oxide catalyst and a sulfonic acid cation exchange catalyst.

Patent Cooperation Treaty Publication (WO) 2008/103480 (Peterson, et al.) relates to conversion of sugars, biomass or both to hydrocarbons, syngas or other compounds. The conversion includes formation of alcohols or carboxylic acids from biomass and subjecting the alcohols, acids or both to decarboxylation (for carboxylic acids) or dehydration (for alcohols) using a metal catalyst, a metal ion catalyst or a base catalyst. Decarboxylation catalysts include bases such as sodium hydroxide, oxidizing agents such as hydrogen peroxide, hydrogen, metal catalysts (e.g., iron or nickel), acid catalysts (e.g., hydrochloric acid, sulfuric acid or dissolved carbon dioxide), or metal ion (e.g., copper) catalysts.

E. Arceo, et al., in "Rhenium-Catalyzed Didehydroxylation of Vicinal Diols to Alkenes Using a Simple Alcohol as a Reducing Agent," *Journal of the American Chemical Society (JACS) Communications*, Vol. 132-33, p. 11409 (29 Jul. 2020), teach use of an alcohol such as 5-nonanol, 3-octanol or 2-octanol to enhance conversion of a vicinal diol such as 1,2-tetradecanediol to an olefin using dirhenium decacarbonyl as a catalyst.

J. Ziegler, et al., in *Inorganic Chemistry*, Vol. 48 (2008), pp. 9998-10000, provides for use of methyltrioxorhenium in catalytic conversion of epoxides and vicinal diols to olefins with $H_2$ as a reductant.

J. Hine, et al., in "The Mechanism of the Transformation of Vicinal Dihalides to Olefins by Reaction with Iodide Ion," *Journal of the American Chemical Society*, Vol. 77 (1955), p. 365, discusses conversion of vicinal dihalides (e.g., 1,2-dibromobutane) to olefins by reaction with a stoichiometric amount of an iodide ion (e.g., that present in a solution of potassium iodide in methanol).

U.S. Pat. No. 3,957,900 (Weisan, g et al.) provides a method for dehydrating diols into diolefins or monoolefins by contacting the diol with a catalyst consisting of a pyrophosphate and an acid orthophosphate of one or more of lithium (Li), sodium (Na), strontium (Sr) and barium (Ba).

Despite the many approaches to similar or related problems, there remains a need for simple and economical processes to convert vicinal polyols and related compounds to olefins.

In one aspect, this invention is a process for preparing an olefin, comprising subjecting a material selected from the group consisting of vicinal polyols, esters of vicinal polyols, ethers of vicinal polyols, and combinations thereof, to non-reductive dehydroxylation in the presence of a halogen-based catalyst containing at least one halogen atom per molecule, under conditions including the substantial absence of a reductive gas and the presence of a non-reductive gas; a temperature ranging from 50 degrees Celsius (° C.) to 250° C.; a liquid reaction medium; and a ratio of moles of the material to moles of the halogen atoms ranging from 1:10 to 100:1; to form an olefin.

A particular feature of the present invention is use of a catalyst that is halogen-based, and preferably iodine-based. As defined herein, the term "halogen-based" means that the catalyst contains at least one halogen, preferably iodine, atom and ionizes at least partially in an aqueous solution by losing one proton. It is important to note that the definition of "halogen-based" is applied to the catalyst at the point at which it catalyzes the dehydroxylation of the material. Thus, it may be formed in situ in a liquid reaction medium beginning with, for example, elemental iodine ($I_2$), which will react with water or another non-gaseous source of hydrogen present in the reaction to form hydrogen iodide (HI), or may be introduced into the reaction already as a halide acid, for example, as pre-prepared HI. Non-limiting examples include iodine ($I_2$), hydroiodic acid (HI), iodic acid ($HIO_3$), lithium iodide (LiI), and combinations thereof. The term "catalyst" is used in the conventionally understood sense, to clarify that the iodide acid takes part in the reaction but is regenerated thereafter and does not become part of the final product. The halogen-based catalyst is at least partially soluble in the liquid reaction medium.

For example, in one non-limiting embodiment where HI is selected as the halogen-based catalyst, it may be prepared as it is frequently prepared industrially, i.e., via the reaction of $I_2$ with hydrazine, which also yields nitrogen gas, as shown in the following equation.

$$2I_2 + N_2H_4 \rightarrow 4HI + N_2 \qquad \text{[Equation 1]}$$

When this reaction is performed in water, the HI must then be separated, via means such as distillation. Alternatively, HI may be distilled from a solution of NaI or another alkali iodide in concentrated hypophosphorous acid. Another way to prepare HI is by bubbling hydrogen sulfide steam through an aqueous solution of iodine, forming the hydroiodic acid (which can then be distilled) and elemental sulfur (which is typically filtered).

$$H_2S + I_2 \rightarrow 2HI + S \qquad \text{[Equation 2]}$$

Additionally, HI can be prepared by simply combining $H_2$ and $I_2$. This method is usually employed to generate high purity samples.

$$H_2 + I_2 \rightarrow 2HI \qquad \text{[Equation 3]}$$

Those skilled in the art will be able to easily identify process parameters and additional methods to prepare HI and/or other reagents falling within the scope of the invention. It is noted that sulfuric acid will not generally work for preparing HI as it will tend to oxidize the iodide to form elemental iodine.

As used herein the term "material" is used to define the compound being converted by the action of the catalyst in the presence of the non-reductive gas atmosphere under the non-reductive dehydroxylation conditions. This compound may be any vicinal polyol, an ester thereof, or a combination thereof. In many embodiments, the vicinal polyol present or represented in the material has at least 2 carbon atoms, preferably from 2 to 12 carbon atoms, more preferably from 2 to 8 carbon atoms, and most preferably from 2 to 6 carbon atoms. The term "vicinal" means that the polyol has hydroxyl groups on adjacent carbons, and the total number of hydroxyl groups may vary according to the number of backbone carbons. Non-limiting examples of such may include ethylene glycol, 1,2-propylene glycol, ethylene glycol diacetate, glycerol, glycerol diacetate, glycerol triacetate, sorbitol, and combinations thereof. Mixtures of at least two vicinal polyols, esters of vicinal polyols, or a combination thereof can be selected. Such may be intentionally manufactured or purchased as a starting material, or may be a byproduct of another manufacturing process.

The amounts of the material and the catalyst are desirably proportioned for optimized conversion to the olefin or olefins. Those skilled in the art will be aware without further instruction as to how to determine such proportions, but generally a ratio of moles of material to moles of halogen, preferably iodine, atoms ranging from 1:10 to 100:1 is preferred. More preferred is a molar ratio ranging from 1:1 to 100:1; still more preferably from 4:1 to 27:1; and most preferably from 4:1 to 8:1.

Temperature parameters employed in the invention may vary within a range of from 50° C. to 250° C., but are preferably from 100° C. to 210° C. Those skilled in the art will be aware that certain temperatures may be preferably combined with certain molar ratios of material and catalyst to obtain optimized olefin yield. For example, a temperature of at least 180° C. combined with a molar ratio of material to halogenatoms of 6:1 may effect, in some embodiments, especially good yields. Other combinations of temperature and ratio of moles of material to moles of halogen atoms may also produce desirable results in terms of conversion of material and selectivity to desired alkenes. For example, with an excess of HI, temperature may be varied especially within the preferred range of 100° C. to 210° C. to obtain a range of selectivity and conversion percentage at a fixed time of, for example, 3 hours. Processing for a longer time at lower temperature is another embodiment. Those skilled in the art will be aware that alteration of any parameter or combination of parameters may affect yields and selectivities achieved.

In certain particular embodiments, time may range from 1 hour to 10 hours. While a time longer than 10 hours may be selected, such may tend to favor formation of byproducts such as those resulting from a reaction of the olefin with one or more of the reactants. Byproduct formation may be more prevalent in a batch reactor than in a continuous process, although the conversion may be carried out via either method. Conversely, a time shorter than 1 hour may reduce olefin yield.

The inventive process is carried out under a substantially non-reductive atmosphere. In this case the atmosphere is substantially free of hydrogen or any reductive gas, and may desirably include individual members or mixtures of the group including, for example, carbon dioxide, carbon monoxide, nitrogen, noble gases such as argon and xenon, and any combination thereof. Hydrogen, a reductive gas, may therefore be present in the reaction's atmosphere, generally a gas stream, in very low amount, but preferably the total atmosphere is at least 98 wt %, preferably 99 wt %, and more preferably 100 wt %, hydrogen-free. As the term is used herein, "substantial absence" shall be defined as meaning that no more than 2% wt % of the atmosphere is a reductive gas. This amount does not include any water that may be present in the atmosphere. The applied gas pressure desirably ranges from 1 psig (~6.89 KPa) to 2000 psig (~13.79 MPa), and preferably from 50 psig (~344.5 KPa) to 200 psig (~1.38 MPa) is desirable. In many embodiments gas pressures in excess of 2000 psig (~13.79 MPa) provide little or no discernible benefit and may simply increase cost of the process. Alternatively, autogenous pressures may be employed.

The process may generally be accomplished using many of the equipment and overall processing parameter selections that are generally known to those skilled in the art. According to processing parameters selected, it is necessary to include a liquid reaction medium in the process, which is another way of saying that the inventive reaction is carried out in liquid phase. Any of the "materials," as defined hereinabove, may function as both the compound to be converted and a portion of the liquid reaction medium, but in the case of the non-reductive reaction, at least a portion, desirably at least 25 weight percent (wt %), of the liquid reaction medium is water. This is because the water is the source of the hydrogen useful for the catalyst regeneration. In preferred embodiments at least 50 wt % is water, and in more preferred embodiments at least 75 wt % is water. Where an additional, non-aqueous liquid reaction medium, such may be selected from acetic acid, carboxylic and fatty acids, organo chloro compounds, and combinations thereof.

For example, if acetic acid is selected, the first reaction would be anticipated to be the conversion of the polyol into an acetate ester, wherein a majority or all of the hydroxyl groups converted. This would result in the formation of an equivalent quantity of water, which could then be used up in the remainder of the reaction to form the olefin. Thus, the acetic acid would therein function as the solvent, provided it generates the requisite quantity of water, meaning that, overall, the reaction does require water, but that such water may be either externally added or simply generated in situ. Also suitable, therefore, is a carboxylic acid that contains from 2 carbon atoms to 20 carbon atoms, preferably from 8 carbon atoms to 16 carbon atoms, may be selected as a liquid reaction medium. Other organic solvents, such as polyols and dialkyl ethers, may also be selected. Where the material selected for conversion is a vicinal polyol, it may be desirable in some non-limiting embodiments for a minor proportion of the reaction medium to be a carboxylic acid, wherein the polyol is sufficiently miscible such that a reaction between the carboxylic acid and the polyol esterifies at least some of the polyol. This facilitates the conversion of the polyol to an olefin.

Because the solubility of, for example, an iodine-based species of the catalyst in an aqueous reaction medium is relatively low (less than 0.0011 mole of iodine atoms is soluble per liter of water at 20° C.) and because during the course of the reaction the starting material, if not $I_2$, converts to $I_2$ and is later reconverted to the original compound (e.g., HI) as shown in the reaction scheme of Equations 1 through 3, it may be desirable in some embodiments of the invention to include therein a solubility enhancing agent. Such may be any compound that enhances the solubility of the halogen-based catalyst in the aqueous reaction medium, but is preferably selected from certain halide salts such as, for example, potassium iodide (KI), sodium iodide (NaI), lithium iodide (LiI), and combinations thereof. The solubility enhancing additive could also be selected from quaternary ammonium salts, ionic liquids, chlorinated and non-chlorinated organic solvents which solubilize iodine, polyols, and combinations of any of the above. The amount of this solubility enhancing additive is preferably within a range of from 0.1 percent by weight percent (wt %) to 50 wt %, more preferably from 1 wt % to 25 wt % and still more preferably from 2.6 wt % to 10 wt %, each wt % being based upon combined weight of additive(s) and water included in, or serving as, the reaction medium. An alternate means of expressing additive amount is a molar ratio of halogen to additive ($I_2$:additive) within a range of from 1:0.1 to 1:20, more preferably 1:0.5 to 1:10, and still more preferably from 1:1 to 1:4. It is noted that the same compound cannot serve as both the catalyst and the solubility enhancer, given the fact that the catalyst is an acid (by definition, it ionizes at least partially in an aqueous solution by losing one proton), whereas the possible additive selections are not with the exception of lithium iodide. If lithium iodide is selected as both the solubility enhancing agent and the catalyst, it may be desirable to use an amount representing a combination of the amount for the catalyst and the amount for the solubility enhancing agent.

It is noteworthy that the inventive process may be accomplished in either one or two steps. If a two step process is desired, the basic reaction may first be conducted under stochiometric conditions. In this case a relatively low temperature in the range of from 50° C. to 120° C. and a the relatively low (less than 50 psig, ~0.34 MPa) gas pressure are employed. This protocol helps to avoid the formation of byproducts. The regeneration of $I_2$ to HI may then be undertaken in a second step at a higher temperature, in the range of from 180 to 210° C., and under a similar gas pressure.

EXAMPLES

General Experimental Procedure

Use a 300 milliliter (mL), High Pressure HASTELLOY™ C-276 Parr reactor with a glass insert as a reaction vessel. Charge 90 mL of water (DI) or acetic acid (S.D. Fine-Chem Ltd.) into the reactor. Add a known amount of ethylene glycol (EG) (S.D. Fine-Chem Ltd.), 1,2-propylene glycol (PG) (Merck) or glycerol (S.D. Fine-Chem Ltd.) to the acetic acid. Add 4 mL of a 55% (weight/weight) aqueous solution of hydroiodic acid (HI) (Merck) or 3.73 gram (g) $I_2$ to the reactor, then close the reactor and mount it on a reactor stand. Flush void space within the reactor two times with gaseous nitrogen (200 psig, ~1.38 MPa)). Feed $N_2$ into the reactor up to a pressure of 300 psig (~2.07 MPa) and heat reactor contents, with stirring at a rate of 1000 revolutions per minute (rpm) up to a temperature of 210° C. Add sufficient additional $N_2$ to the reactor to increase pressure within the reactor up to 1000 psig (~6.89 MPa). After 45 minutes of reaction time, remove a sample of vapor phase within the reactor using a gas sampling vessel. Analyze the sample via gas chromatography (GC) (Agilent 7890 with two thermal conductivity detectors (TCDs) and one flame ionization detector (FID)). Use a PoraPlot™ Q (Varian™ CP7554) column to separate carbon dioxide ($CO_2$), olefins and alkanes. Use a CP Wax (Varian™ CP7558) column to separate oxygenates and a molecular sieve (Molsieve™) (Varian™ CP7539) column to separate hydrogen, nitrogen and lower hydrocarbons. Allow the reaction to continue for 6 hours.

Calculate mole percent (mol %) conversion of material to olefin from vapor phase composition data according to the following equation:

$$\text{mole \%} = \left[ \frac{\frac{\text{vol \%}}{100} \times \frac{\text{total pressure}}{14.7} \times \frac{\text{volume of gas}}{22400}}{\text{moles of material}} \right] \times 100 \quad [\text{Equation 4}]$$

Example 1

Using the above General Experimental Procedure with 0.19 mole EG, 0.015 mole $I_2$, a temperature of 210° C., acetic acid, 90 mL, and a time of 6 hours, effect a 42% conversion of EG with a product stream selectivity of 77 percent by weight (wt %) ethylene and 23 wt % carbon dioxide ($CO_2$), each wt % being based upon total product stream weight.

Example 2

Replicate Example 1, but substitute 0.1 mole of ethylene glycol diacetate (EGDA) for the EG. Again, reaction is in acetic acid, 90 mL. This Example 2 effects 23 wt % conversion of the EGDA with a product stream selectivity of 85 wt % ethylene, 2 wt % ethane and 13 wt % $CO_2$, each wt % being based upon total product stream weight.

Example 3

Replicate Example 1, but change the amount of EG to 0.21 mol, the time to 5 hours and use water in place of acetic acid. This Example 3 effects 71% conversion of the EG with a product stream selectivity of 89 wt % ethylene and 11 wt % $CO_2$, each wt % being based upon total product stream weight.

Example 4

Replicate Example 3, but reduce the amount of EG to 0.18 mole and add 0.06 mole of potassium iodide to the water. This Example 4 effects 99% conversion of the EG with a product stream selectivity of 84 wt % ethylene and 16 wt % $CO_2$, each wt % being based upon total product stream weight.

Comparative Example A

Replicate Example 1, but change the amount of EG to 0.18 mole, and introduce 100 psig (~0.69 MPa) hydrogen in place of the 300 psig (~0.69 MPa nitrogen). This Comparative Example A effects 60% conversion of the EG with a product stream selectivity of 94 wt % ethylene, 1 wt % ethane, and 5 wt % $CO_2$, each wt % being based upon total product stream weight.

The invention claimed is:

1. A process for preparing an olefin comprising:
   subjecting a material to a dehydroxylation in presence of an iodine-based catalyst and a liquid reaction medium comprising water to form an olefin;
   wherein the material is selected from the group consisting of vicinal polyols, esters of vicinal polyols, ethers of vicinal polyols, and combinations thereof;
   wherein the iodine-based catalyst is selected from the group consisting of $I_2$ (iodine), HI (hydroiodic acid), LiI (lithium iodide) and combinations thereof; and
   wherein the process is operated under conditions including:
      a non-reductive atmosphere having no more than 2 weight percent of a reductive gas, excluding hydrogen present in atmospheric water, if any;
      a temperature ranging from 50° C. to 250° C.; and
      a ratio of moles of the material to moles of the iodine atoms in the iodine-based catalyst ranging from 4:1 to 27:1.

2. The process of claim 1, wherein the non-reductive atmosphere includes a non-reductive gas that is selected from the group consisting of nitrogen, carbon monoxide, carbon dioxide, argon, xenon, and combinations thereof.

3. The process of claim 2, wherein the non-reductive gas is at a pressure ranging from 1 psig (~6.89 kPa) to 2000 psig (~13.79 MPa) or at autogenous pressure.

4. The process of claim 1, wherein the temperature ranges from 100° C. to 210° C.

5. The process of claim 1, wherein the ratio of moles of the material to moles of the iodine atoms ranges from 6:1 to 27:1.

6. The process of claim 1, wherein the conditions include carrying out the dehydroxylation in the liquid reaction medium including water and a second material selected from the group consisting of acetic acid, fatty acids, organo chloro compounds, dialkyl ethers, and combinations thereof.

7. The process of claim 6, wherein the liquid reaction medium includes water, the second material, and a solubility enhancing agent selected from the group consisting of potassium iodide, sodium iodide, lithium iodide, quaternary ammonium salts, ionic liquids, chlorinated and non-chlorinated organic solvents, polyols, and combinations thereof, the solubility enhancing agent serving to enhance the solubility of the iodine-based catalyst in the liquid reaction medium.

* * * * *